United States Patent
Chikami (12)

(10) Patent No.: US 6,332,774 B1
(45) Date of Patent: Dec. 25, 2001

(54) RETAINER WIRE AND TOOTH ROW RETAINING DEVICE USING RETAINER WIRE

(75) Inventor: Kunio Chikami, Kochi (JP)

(73) Assignee: Chikami Miltec Inc., Kochi (JP)

( * ) Notice: Subject to any disclaimer, the term of this patent is extended or adjusted under 35 U.S.C. 154(b) by 0 days.

(21) Appl. No.: 09/582,269

(22) PCT Filed: May 17, 1999

(86) PCT No.: PCT/JP99/02557

§ 371 Date: Jun. 23, 2000

§ 102(e) Date: Jun. 23, 2000

(87) PCT Pub. No.: WO00/54695

PCT Pub. Date: Sep. 21, 2000

(30) Foreign Application Priority Data

Mar. 18, 1999 (JP) .................................................. 11-001648

(51) Int. Cl.[7] .............................................................. A61C 3/00
(52) U.S. Cl. ...................................................... 433/20; 433/6
(58) Field of Search ................................................ 433/6, 20

(56) References Cited

U.S. PATENT DOCUMENTS

| 4,413,978 | 11/1983 | Kurz | 433/6 |
| 5,096,416 | 3/1992 | Hulsink | 433/6 |
| 5,454,716 | * 10/1995 | Banerjee et al. | 433/62 |
| 5,536,169 | 7/1996 | Yousefian | 433/6 |
| 5,607,300 | * 3/1997 | Tepper | 433/62 |

FOREIGN PATENT DOCUMENTS

| 2-109552 | 4/1990 | (JP) . |
| 6-509008 | 10/1994 | (JP) . |
| 7-213538 | 8/1995 | (JP) . |

* cited by examiner

*Primary Examiner*—Cary E. O'Connor
(74) *Attorney, Agent, or Firm*—Armstrong, Westerman, Hattori, McLeland & Naughton, LLP

(57) ABSTRACT

An object of the present invention is to provide a retainer wire which can solve problems of a conventional retainer wire and improve the extractive strength of the joint portion of a plastic portion and a metal wire portion. The present invention is directed to retainer wire including: a holding portion formed in the shape of a circular arc so as to be able to be in contact with a dentitition; and a metal wire metal extended from both ends of said holding, portion; wherein said holding portion is made of a synthetic resin having transparency and a specified mechanical strength; and wherein the supporting portion is formed together with the holding portion into one body.

8 Claims, 11 Drawing Sheets

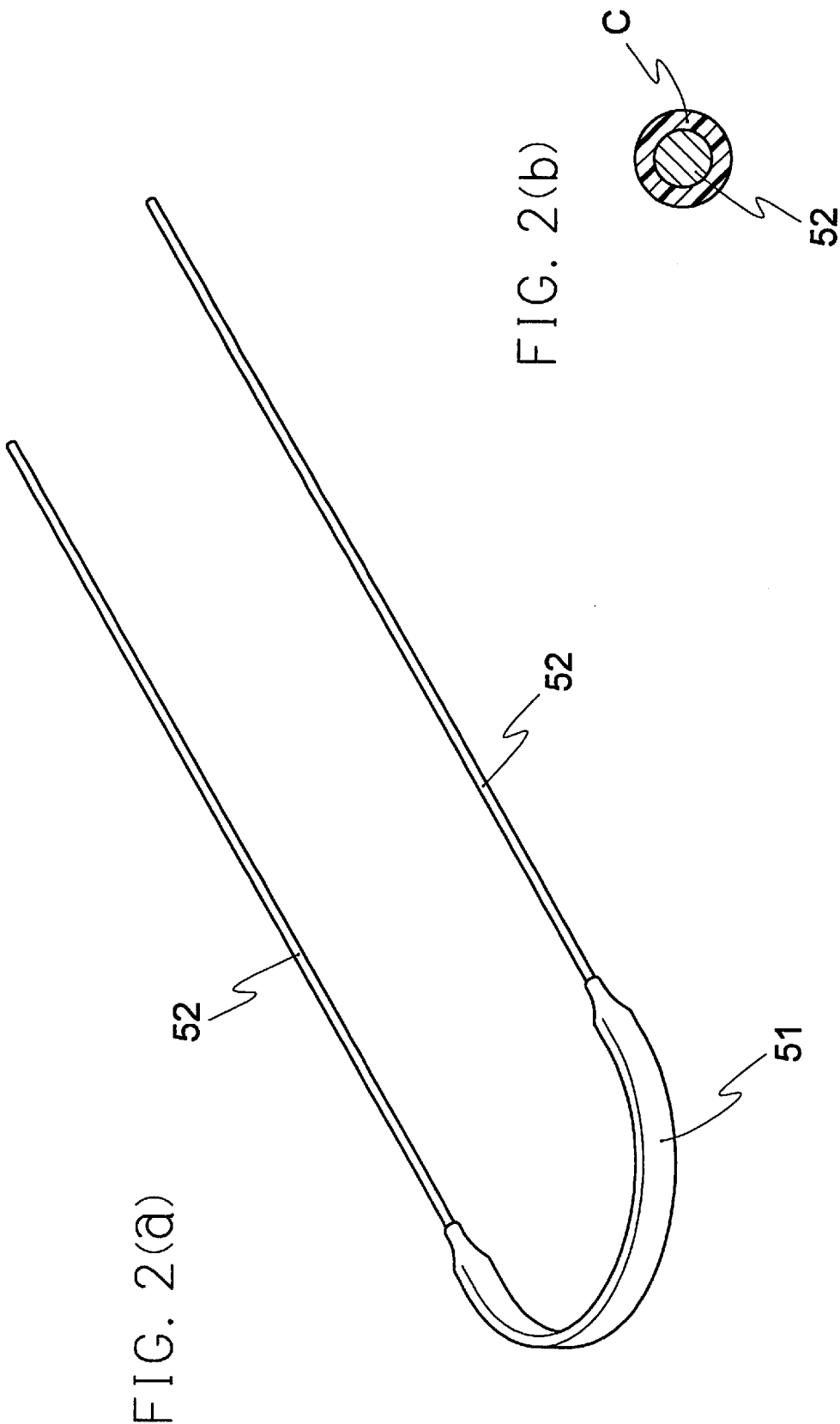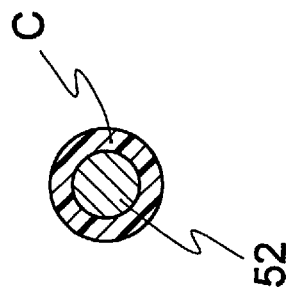

RETAINER WIRE AND TOOTH ROW RETAINING DEVICE USING RETAINER WIRE

TECHNICAL FIELD

The present invention relates to a dentition retaining appliance. More particularly, the present invention relates to a dentition retaining appliance which is composed of a base part to be stuck closely to the upper or lower surface of the palate and to the root portion of each tooth at the reverse side of a dentition, and a holding means whose end portions are fixed to said base part, and which holds a desired dentition by pressing corrected teeth between said base part and said holding means.

BACKGROUND ART

A retainer wire made of metal to be used in a dentition retaining appliance has been known up to now (hereinafter referred to as "prior art 1"). A retainer wire 10 of the prior art 1 (see FIG. 4), whose end portions both are fixed to the front end of a base part 1, is formed in the shape of a loop and is mounted so as to enclose a plurality of teeth including a corrected tooth (see FIG. 7).

And since a corrected tooth has the retainer wire 10 attached to it in the shape of a loop, even if it attempts to return to the state where it is not corrected, a reactive force is generated in the retainer wire 10 and therefore the corrected tooth is pressed against the base part 1. Since the state of a corrected dentition is kept in this way, it is prevented that the dentition is twisted or inclined similarly to its original state.

In case of a retainer (hereinafter referred to as a "retaining appliance" also) made using a retainer wire 10 of prior art 1 which is composed only of a metal wire, there is a disadvantage that the metal wire comes into a state where it is stuck to the surface of a dentition of front teeth as it is naked and when the mouth is loosened this metal wire results in being seen.

Originally, it is desired for a retainer to be equipped for twenty-four hours, but in many cases a retainer of a metal wire is not continuously equipped because it is not nice to look at, and therefore, a problem is pointed out that since a dentition once corrected% attempts to return to the original state, a period of remedy is made long.

And in order to make a metal wire be along the surface of a dentition, it is necessary to apply a bending process to it using a pair of pliers (pincers).

As a retainer wire capable of solving such a problem, the present inventor has proposed a retainer wire used in a retaining appliance as shown in FIGS. 10 and 11 in Japanese Unexamined Patent Publication No. 213538/1995 (hereinafter referred to as "prior art 2").

A retaining appliance (retainer wire) shown on 10 is composed of a base part 1 which is adapted to the shape of the lower jaw part in the palate and is stuck closely to the reverse surface of a dentition, a holding portion 2b and a spring portion 9a which are made of synthetic resins and are fixed to the front end of the base part 1, and a supporting portion 3 composed of metal wires provided in the left and right rear ends of the base part 1.

Prior to making a retaining appliance, first a model of the lower or upper jaw part in the palate of a patient is made. For example, a model of the lower or upper jaw is made in gypsum, and then a holding portion 2b and a supporting portion 3 are attached onto the said model.

Finally, metal wires are attached to models of the left and right molar teeth to form the supporting portion 3. One end of this wire is also extended at the reverse side of a dentition.

When a holding portion and a supporting portion 3 have been attached to a model of a dentition in such a way, a molten acrylic resin is poured into the model to form a base part 1. When it has been left as it is for several minutes or longer, a retaining appliance in which a saddle-shaped base part 1 has a holding portion 2b and a supporting portion 3 fixed to it can be obtained.

Such a material being resistant to various bacteria or stains in the oral cavity as an acrylic resin is adopted as a material for the base part 1. The thickness of the base part 1 is set at about 0.5 to 1.0 mm.

And as materials for the holding portion 2 and the spring portion 2a, materials which have a thermal contractility and a shape memory due to a heating temperature in the past, are comparatively high in bending strength and in tensile strength, and are resistant to various bacteria or stains in the oral cavity such as polyethylene terephthalate, polybuthylene terephthalate, polycarbonate, copolymer of cyclohexadimethanol-terephthalate and the like are adopted.

As the shape and the size of a holding portion 2, in addition to a circle having a diameter of about 0.5 to 5.0 mm in section, a rectangle or a flat plate having a section of about "(0.3 to 5.0)×(0.5 to 10.0) mm" is used.

Further, Japanese Unexamined Patent Publication No. 213538/1995 has disclosed a retaining appliance in which a portion 10a adjacent to a spring portion 2a and the other end 10b of a supporting portion 3 are joined to each other by caulking (see FIGS. 5, 6 and 11).

In this way, a retainer wire 10 of prior art 2 uses a transparent plastic resin and in case of a retainer 20 made using this retainer wire 10, since a transparent plastic member is mounted on the surface of a dentition of a front tooth part and the transparent plastic member is only seen even if the mouth is loosened, it is hardly known that the retaining appliance is equipped. Therefore, there is an advantage that since a patient is continuously equipped with it without being concerned about its appearance, the period of remedy is made short.

As a retainer wire of prior art 2 there are two kinds in which one is a retainer wire being made of plastics as a whole (see FIGS. 9 and 10) as described above (since it is made of plastics as a whole, in case that some looseness occurs between a tooth model, and a spring portion 2 and a supporting portion 3, a correcting process to be performed as heating at a high temperature is needed for amendment and the other is a joint-type retainer wire in which only the front tooth part being seen is made of transparent plastics and the part being not seen is made of a conventional metal wire as shown in FIG. 11 (some looseness between a tooth model, and a spring portion 2 and a supporting portion 3 or supporting portion 2c (FIG. 8) can be corrected only by a pair of pliers or the like without heating).

In order to make a metal wire be along the surface of a dentition, it is enough to correct it using a pair of pliers (pincers) or the like, but in order to make a plastic wire, which is a retainer wire of prior art 2 using plastics set by heating, be along the surface of a dentition, it is necessary to heat it at a high temperature and then correct it using a pair of pliers (pincers) or the like.

And in case of making a retainer using a joint-type retainer wire, it is necessary to physically join to each other and use two members which are a plastic portion 2 of a front tooth part (hereinafter referred to as a "holding portion"), and a metal wire of a spring portion 2 and a supporting portion 3.

An object of the present invention is to provide a retainer wire which can solve said problems of a conventional retainer wire and improve the extractive strength of the joint portion of a plastic portion and a metal wire portion.

DISCLOSURE OF INVENTION

A retainer wire which is a first embodiment of the present invention is characterized by a retainer wire comprising;

a holding portion formed in the shape of a circular arc so as to be able to be in contact with a dentition, and a supporting portion made of metal extended from both ends of said holding portion, wherein;

said holding portion is made of a synthetic resin having transparency and a specified mechanical strength, and said supporting portion is formed together with said holding portion into one body.

A dentition retaining appliance which is a second embodiment of the present invention is characterized by a dentition retaining appliance composed of a retainer wire whose ends both are fixed to a base part and which is hitched around in the shape of a loop so as to enclose a plurality of teeth including a corrected tooth, wherein said retainer wire is composed of said retainer wire.

BRIEF DESCRIPTION OF DRAWINGS

FIG. 2 is a perspective view and sectional view showing a state where a retainer wire of one embodiment of the present invention has just been subjected to an injection molding;

BEST MODE FOR CARRYING OUT THE INVENTION

A retainer wire of the present invention is described in detail with reference to the accompanying drawings.

Figure 1:
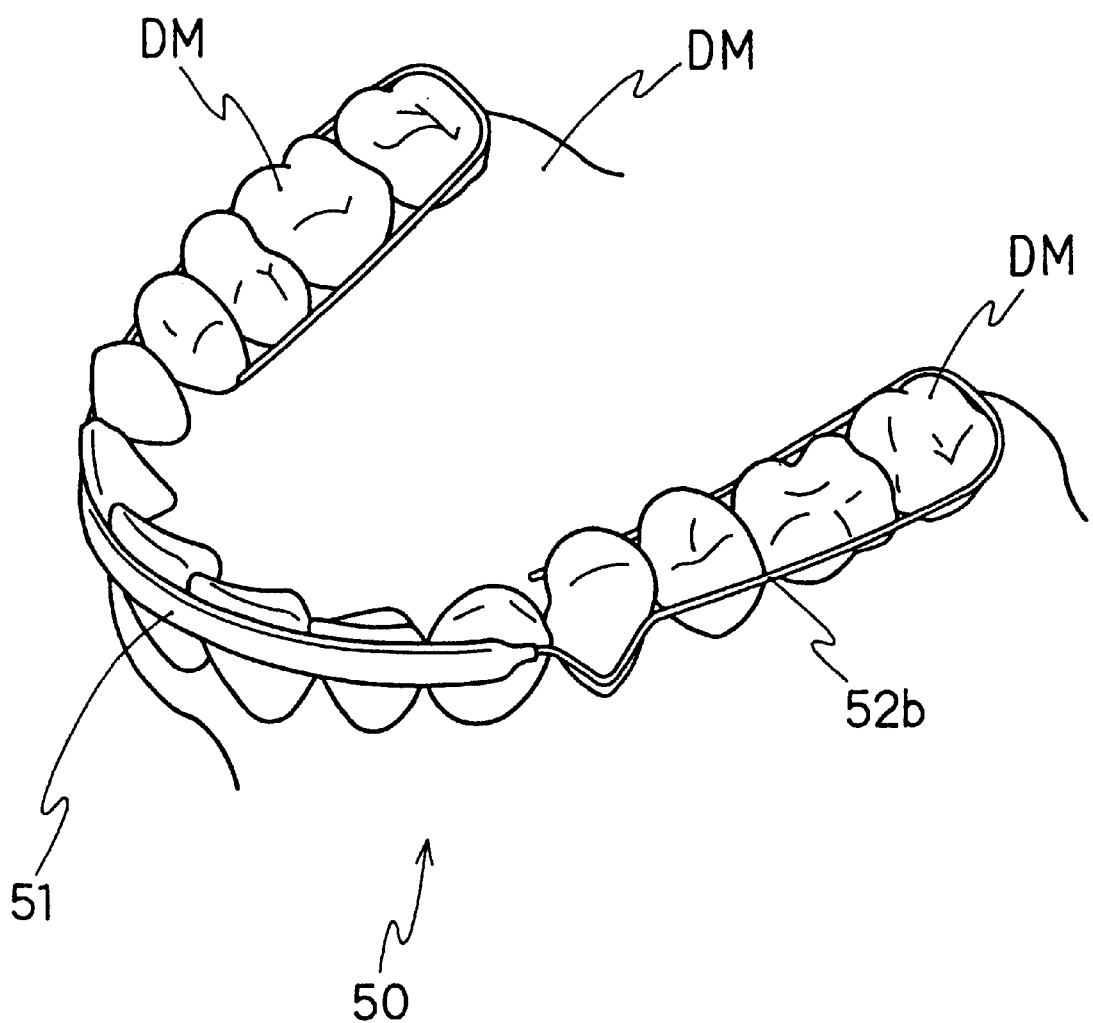
FIG. 1 is a perspective view showing a state where a retainer wire of an example of one embodiment of the present invention is mounted on a dentition of a tooth model.
Figure 3:
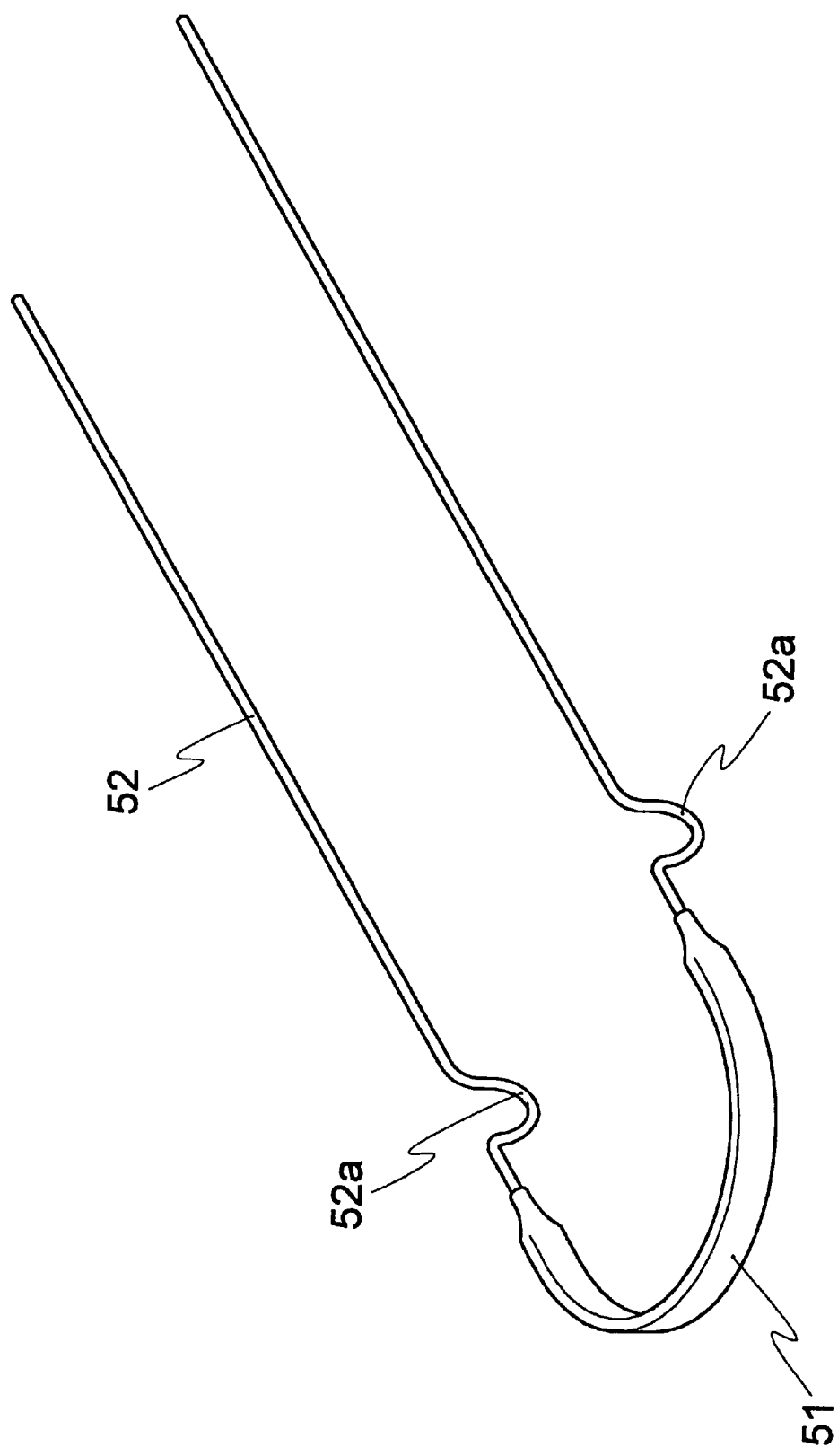
FIG. 3 is a perspective view showing a state where a spring portion is formed in the retainer wire of FIG. 2.
Figure 4:
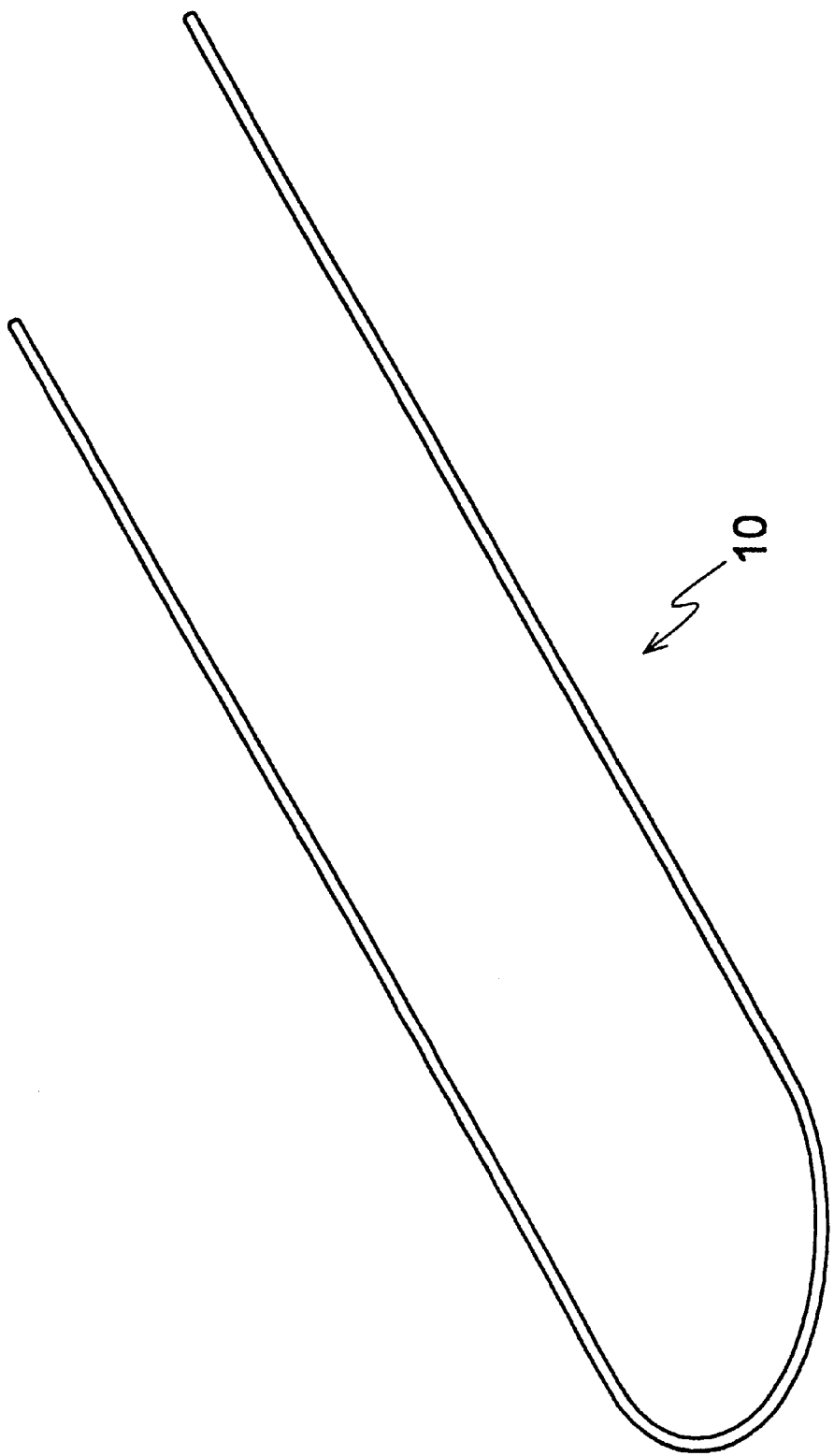
FIG. 4 is a perspective view showing one example of conventional retainer wire.
Figure 5:
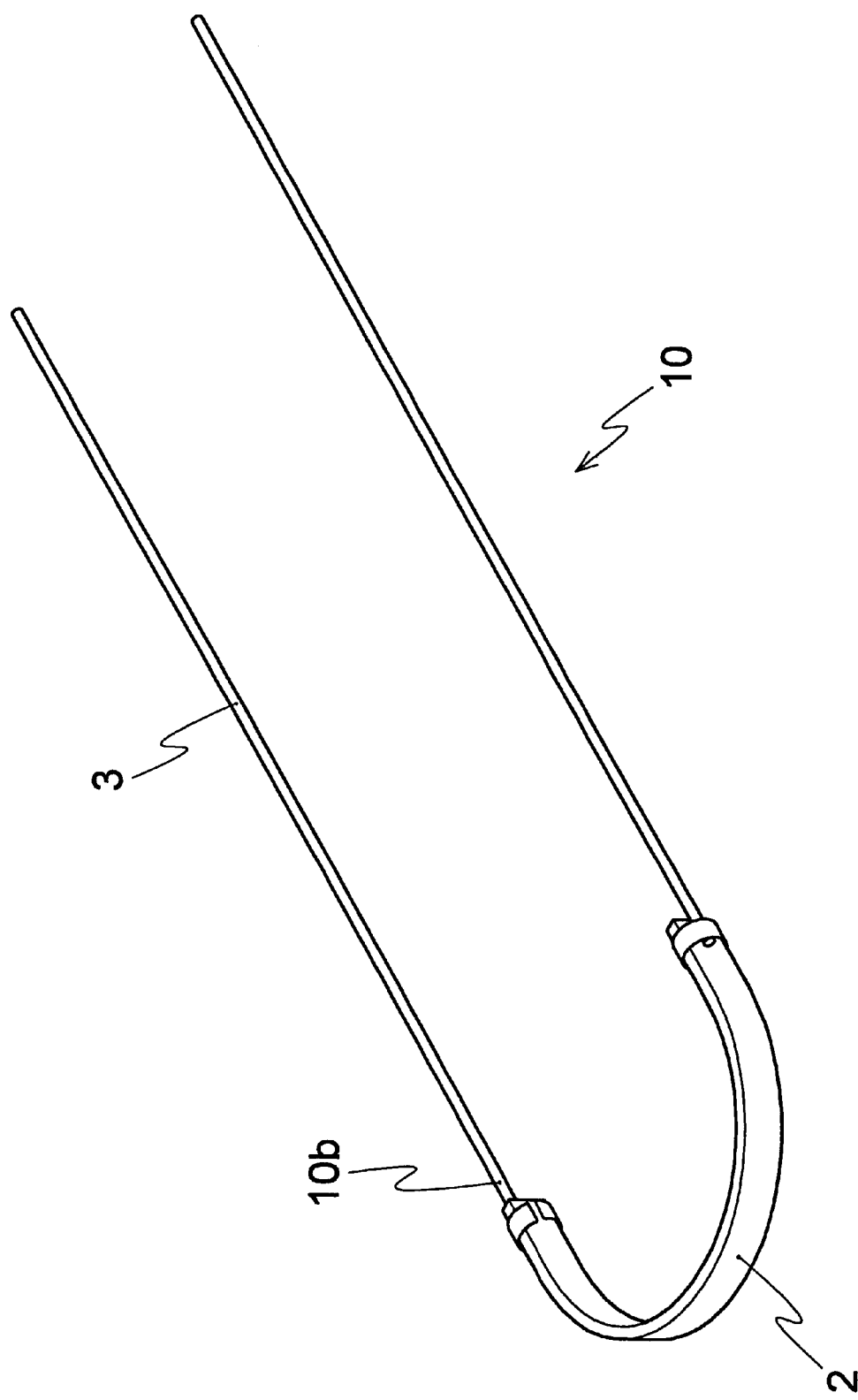
FIG. 5 is a perspective view showing the other example of conventional retainer wire.
Figure 6:
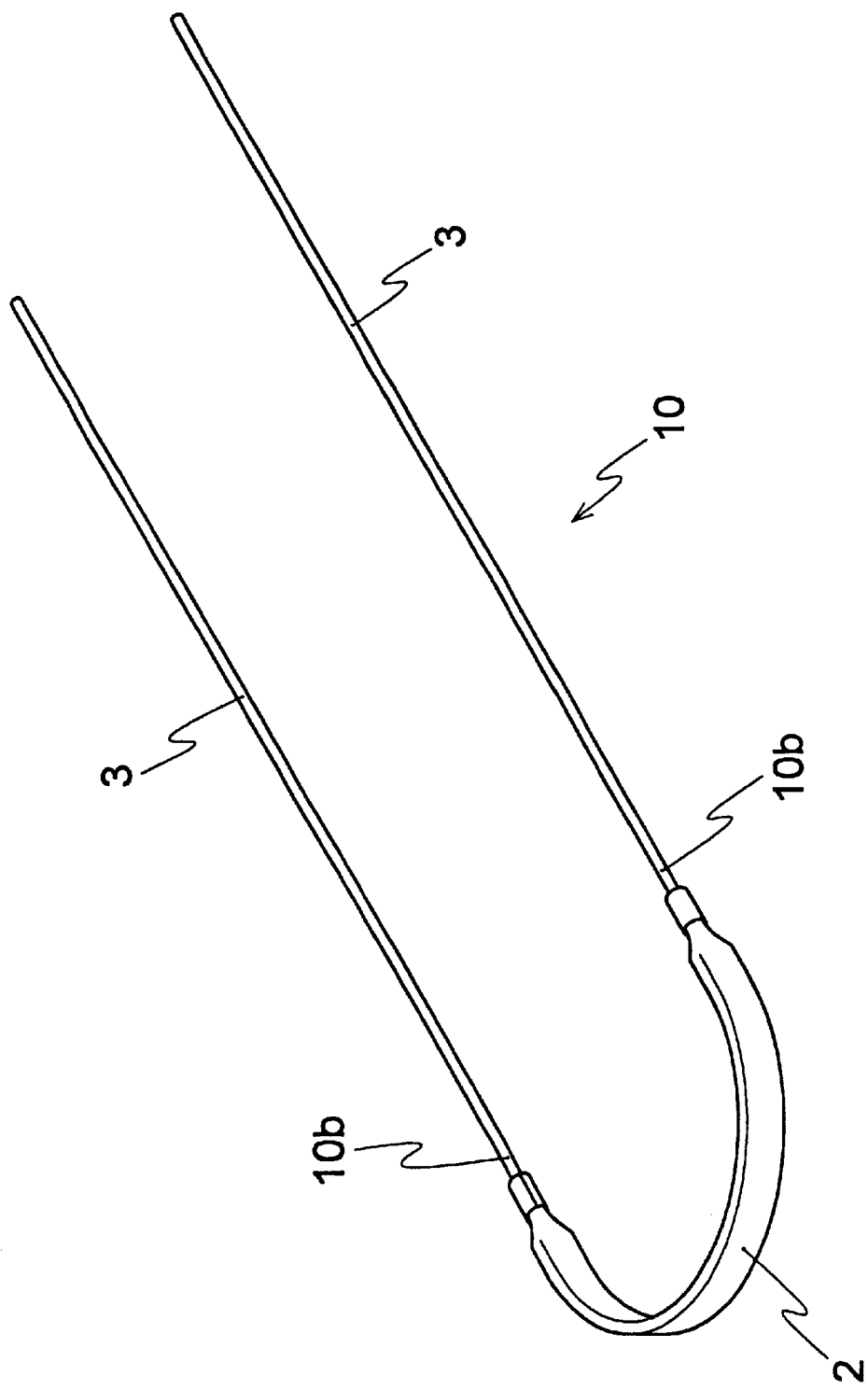
FIG. 6 is a perspective view showing still other example of conventional retainer wire.
Figure 7:
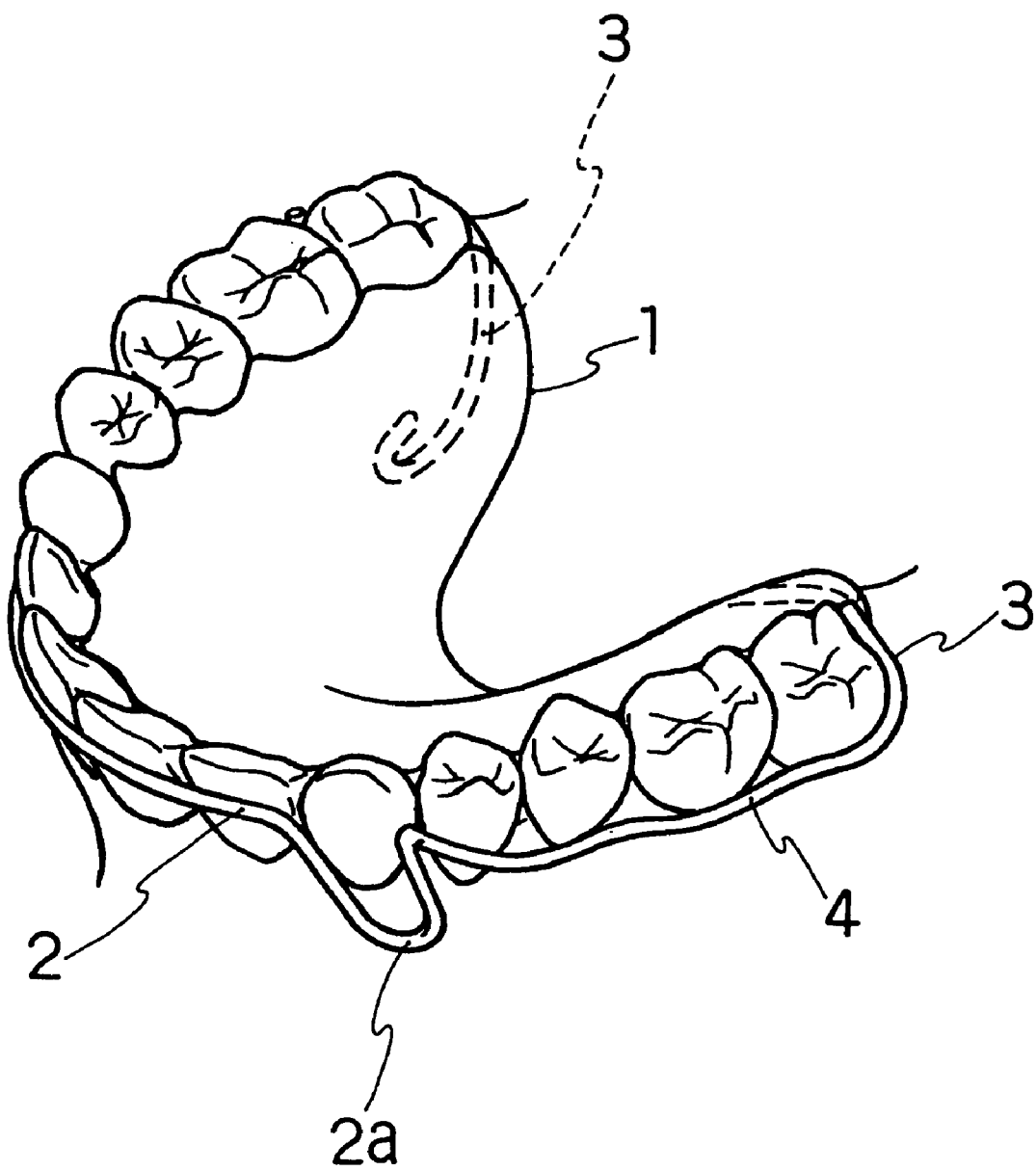
FIG. 7 is a perspective view showing a state where conventional dentition retaining appliance is mounted on the dentition.
Figure 8:
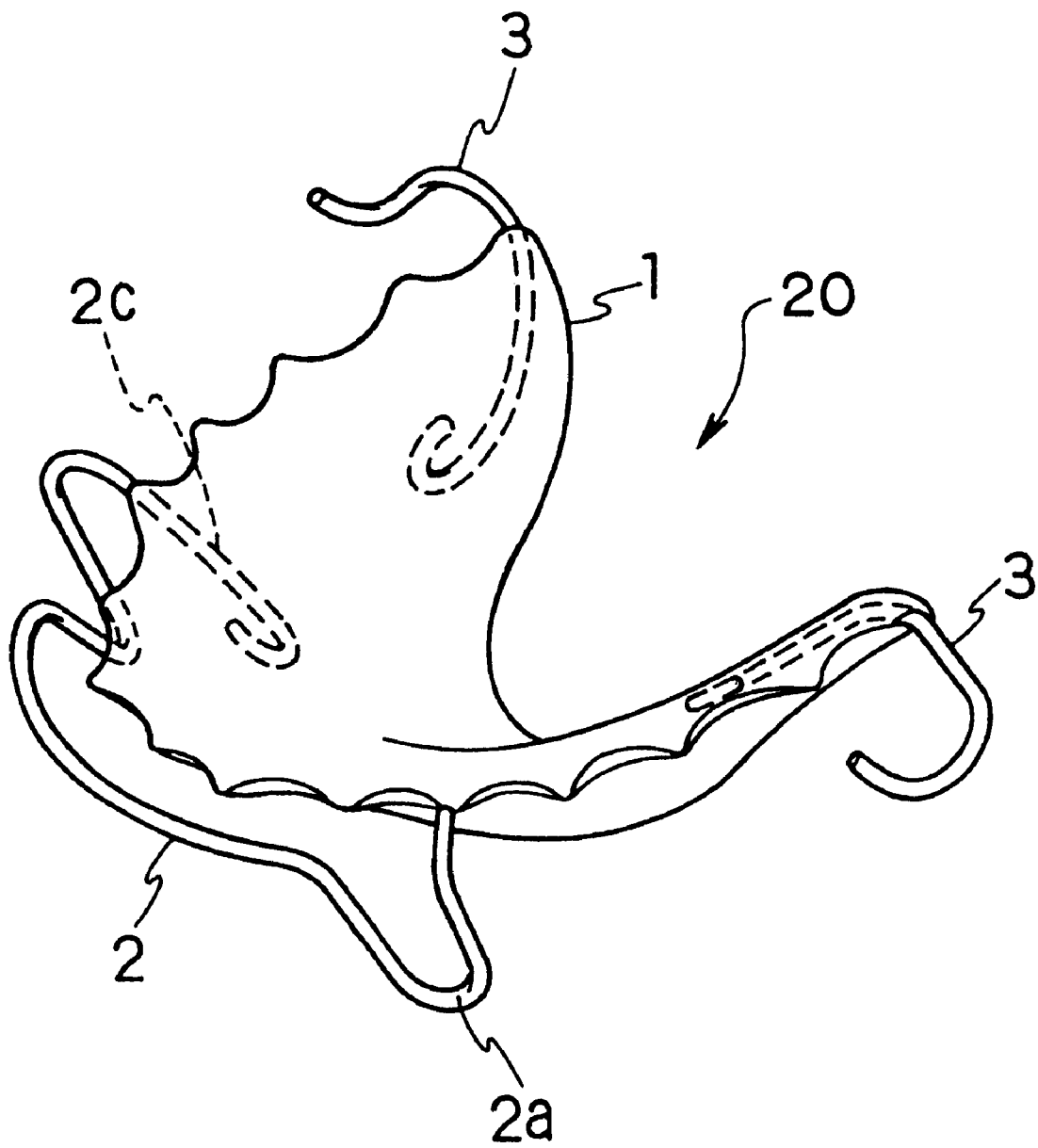
FIG. 8 is a perspective view showing a state where the dentition retaining appliance is removed from the dentition.
Figure 9:
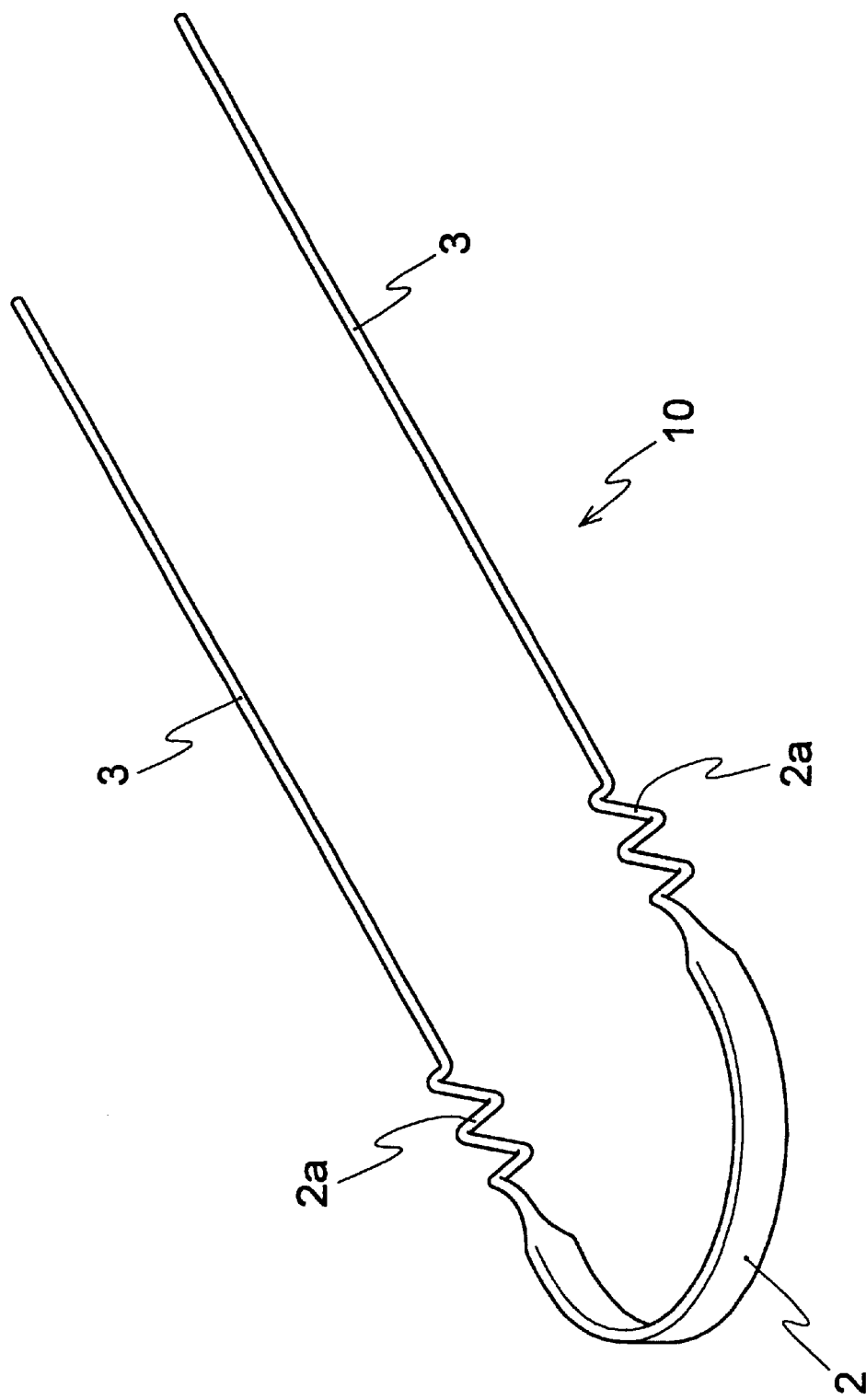
FIG. 9 is a perspective showing one example of conventional retainer wire.
Figure 10:
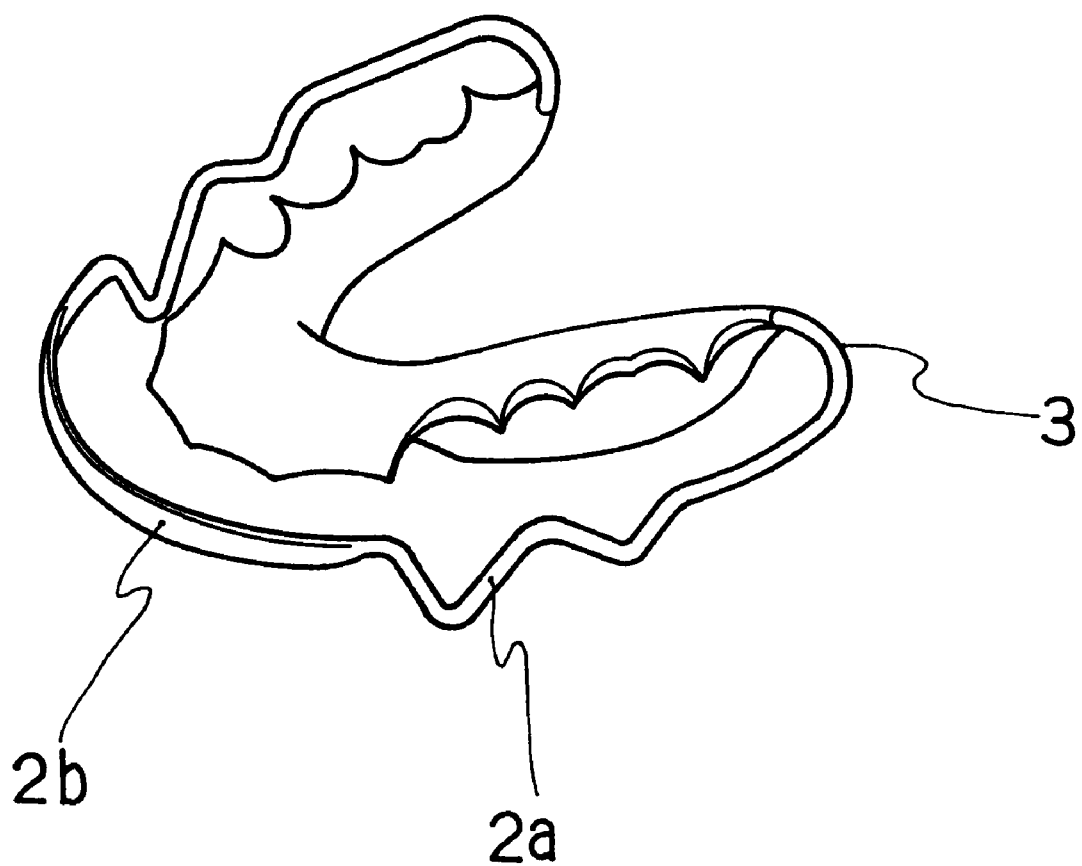
FIG. 10 is a perspective view of conventional dentition retaining appliance.
Figure 11:
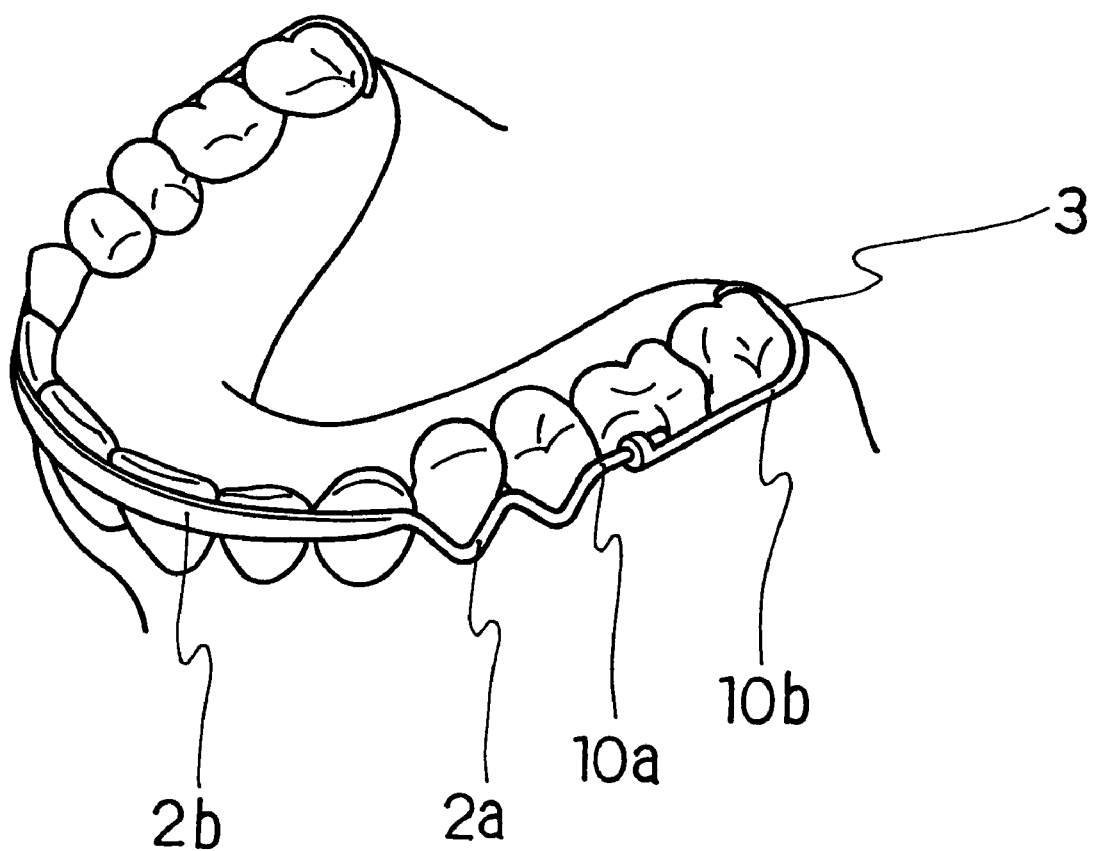
FIG. 11 is a perspective view showing a state where the dentition retaining appliance of FIG. 10 is mounted on the dentition.

FIG. 1 is a perspective view showing a state where an example of a retainer wire according to an embodiment of the present invention is mounted on a dentition of a tooth model, FIG. 2 is a perspective view showing a state of a retainer wire according to an embodiment of the present invention, and FIG. 3 is a perspective view showing a state where a spring portion is formed in the retainer wire of FIG. 2.

As shown in FIG. 1, a retainer wire 50 according to this embodiment is composed of a holding portion 51 in the shape of a circular arc to be put on a portion equivalent to front teeth of the dentition and a metal wire 52 fixed to the holding portion 51.

The metal wire 52 comprises a spring portion 52a and a supporting portion 52b.

Fixing the metal wire 52 to the holding portion 51 is achieved by burying an end portion of the metal wire 52 into the holding portion 51.

In comparison with a conventional retainer wire, a retainer wire of the present invention formed as described above has two members of a plastic portion (holding portion 51) of a front tooth portion and a metal wire 52 of a spring portion 52a and a supporting portion, said two members being joined to each other into one body in advance (namely, an end portion of the metal wire 52 has been buried into the plastic member to function as the holding portion 51), and therefore it is more greatly improved in extractive strength of the joint portion than the conventional retainer wire joining the two members to each other in a later process, and variation in joining strength due to a joining technique of a manufacturer is solved and a uniform extractive strength can be obtained. In this connection, while the prior art gives an extractive strength of about 3.0 kg, the present invention gives about 9.0 kg. And when making a retainer, a process of physically joining two members to each other which are a plastic portion of a front tooth part (holding portion 51) and a metal wire 52 of a spring portion 52a and a supporting portion 52b is unnecessary.

And a retainer wire according to the present invention is thermally deformed by thermal contraction of plastics.

Therefore, in order to make a retainer, when a retainer wire 50 of the present invention is set softly along a tooth model in advance and is heated at a specified or higher temperature (where either wet heating or dry heating may be used), the plastic portion (holding portion 51) of the retainer wire 50 is thermally contracted and is easily made to be along the surface of the dentition of the tooth model. Depending upon selection of a resin to be used, when a retainer wire 50 being in a state where it is softly fixed along a tooth model DM (see FIG. 1) is left in boiling water for about 1 second to 30 minutes, a plastic portion is easily made to be along the tooth model DM by a thermal contraction to bring a fine finish.

Thanks to this, a conventional correcting process of making a plastic wire be along the surface of a tooth model by means of a pair of pliers (pincers) or the like has become unnecessary. Due to this, a working time for making a retainer can be greatly shortened.

As described above, a retainer wire of the present invention made of a thermoplastic resin is set softly along a tooth model and the synthetic resin is thermally contracted by being given a temperature equal to or higher than a contraction temperature of the respective resins, and thereby it is possible to easily make a retainer whose plastic portion is finely along a tooth model.

As for a heating temperature, either dry heating or wet heating may be used but the use of wet heating is easier and more preferable in order to obtain a more uniform contraction. In case of utilizing a wet heating process, it is possible to easily generate a uniform thermal contraction, using a wet heating process by changing a boiling temperature through applying pressure and changing an air pressure or through applying some auxiliary agent such as salt and the like. And it is a matter of course that it is possible also to generate a thermal contraction using a dry heating means such as a hot air furnace and the like.

In comparison with a conventional retainer wire, a retainer wire of the present invention has a plastic portion and a metal wire joined into one body and saves the trouble to join the two members at the time of making a retainer and thereby makes it possible to greatly shorten the working time and greatly improve the joining strength.

And since a retainer of the present invention is thermally contracted and is made to be along a tooth model by heating at a comparatively low temperature, the working time is greatly shortened and a retainer better fitted to the tooth model can be easily made. A material for the metal wire is selected from materials having corrosion resistance and being easily given a plastic processing, and for example stainless steel, nickel-cobalt alloy, nickel-chromium alloy, titanium alloy and the like are preferably adopted.

And as shown in FIG. 2(b), an effect good for a metal-allergy patient can be obtained by using a metal wire 52 provided with a coating layer C obtained by applying a coating process such as synthetic resins, ceramics and the like to its surface. In this case a coated wire 52 may be used, or after the product has been finished its metal wire may be coated.

According to a retainer wire of the present invention the extractive strength of the joint portion of a plastic portion and a metal wire is greatly improved. And a retaining appliance using a retainer wire of the present invention can be not only easily made but also better fitted to a tooth model.

INDUSTRIAL APPLICABILITY

In a retainer wire of the present invention, a part being most conspicuous when being put on teeth is made of transparent plastics and the extractive strength of the joint portion of this plastic portion and the metal wire is more greatly improved in comparison with a conventional retainer wire. Therefore, it is useful as an orthodontic appliance for dentistry to be used in orthodontics.

What is claimed is:

1. A retainer wire, comprising:

a holding portion formed in the shape of a circular arc so as to be in contact with a dentition, said holding portion having two ends, and said holding portion being made of a synthetic resin having transparency and a specified mechanical strength; and two metal wires, an end of each metal wire being buried into a respective end of said holding portion.

2. The retainer wire of claim 1, wherein said metal wire is provided with a coating layer.

3. A dentition retaining appliance comprising the retainer wire of claim 2, and a base part;

wherein both ends of the retainer wire are fixed to the base part; and wherein the retainer wire is hitched around in the shape of a loop so as to enclose a plurality of teeth including a corrected tooth.

4. A dentition retaining apparatus comprising the retainer wire of claim 1, and further comprising a base part;

wherein the non-buried ends of the metal wires are fixed to the base part; and wherein the retainer wire is hitched around in the shape of a loop so as to enclose a plurality of teeth including a corrected tooth.

5. The retainer wire of claim 1, said metal wires each comprising a spring portion and a supporting portion.

6. The retainer wire of claim 1, the extractive strength of each metal wire from the holding portion being greater than 3.0 kg.

7. The retainer wire of claim 1, the extractive strength of each metal wire from the holding portion being at least 9.0 kg.

8. The retainer wire of claim 1, said holding portion having a cross section which is rectangular with a first dimension in the range of 0.3 to 5.0 mm and a second dimension in the range of 0.5 to 10.0 mm.

* * * * *